(12) United States Patent
Vaz et al.

(10) Patent No.: US 10,383,590 B2
(45) Date of Patent: Aug. 20, 2019

(54) METHODS AND SYSTEMS FOR ADAPTIVE SCAN CONTROL

(71) Applicant: General Electric Company, Schenectady, NY (US)

(72) Inventors: Michael Sarju Vaz, Milwaukee, WI (US); Elizabeth Janus Nett, Wauwatosa, WI (US); David Joseph Pitterle, Waukesha, WI (US); David Erik Chevalier, Menomonee Falls, WI (US); Christine Carol Hammond, Oconomowoc, WI (US); Chelsey Lewis, Seattle, WA (US)

(73) Assignee: General Electric Company, Schenectady, NY (US)

( * ) Notice: Subject to any disclaimer, the term of this patent is extended or adjusted under 35 U.S.C. 154(b) by 537 days.

(21) Appl. No.: 14/868,146

(22) Filed: Sep. 28, 2015

(65) Prior Publication Data

US 2017/0086772 A1    Mar. 30, 2017

(51) Int. Cl.
*A61B 6/03*    (2006.01)
*A61B 6/00*    (2006.01)

(52) U.S. Cl.
CPC .............. *A61B 6/504* (2013.01); *A61B 6/032* (2013.01); *A61B 6/481* (2013.01); *A61B 6/486* (2013.01);
(Continued)

(58) Field of Classification Search
CPC ......... A61B 6/542; A61B 6/032; A61B 6/481; A61B 6/504; A61B 6/507; A61B 6/54
(Continued)

(56) References Cited

U.S. PATENT DOCUMENTS 5,459,769 A * 10/1995 Brown .................... A61B 6/032
378/16
5,594,772 A * 1/1997 Toki ..................... A61B 5/0456
378/114
(Continued)

FOREIGN PATENT DOCUMENTS

CA    2884606 A1    3/2014
EP    2189112 A1    5/2010
(Continued)

OTHER PUBLICATIONS

International Search Report and Written Opinion for corresponding PCT application PCT/US2016/038391 dated Sep. 22, 2016; 12 pages.
(Continued)

*Primary Examiner* — Allen C. Ho
(74) *Attorney, Agent, or Firm* — McCoy Russell LLP

(57) ABSTRACT

Methods and systems are provided for adaptive scan control. In one embodiment, a method comprises: while performing a scan of a scan subject, processing acquired projection data to measure a contrast level; responsive to the contrast level increasing above a first threshold, automatically switching the scan from a first scan protocol to a second scan protocol; responsive to the contrast level decreasing below a second threshold, automatically switching the scan from the second scan protocol to the first scan protocol; and responsive to the contrast level decreasing below a third threshold, automatically ending the scan. In this way, multiple scan protocols, such as angiography and perfusion scan protocols, can be interleaved within a single scan without the use of a separate timing bolus scan.

18 Claims, 6 Drawing Sheets

(52) U.S. Cl.
CPC ............. *A61B 6/501* (2013.01); *A61B 6/507* (2013.01); *A61B 6/5217* (2013.01); *A61B 6/54* (2013.01); *A61B 6/542* (2013.01)

(58) Field of Classification Search
USPC ...................... 378/15, 62, 115, 116
See application file for complete search history.

(56) References Cited

U.S. PATENT DOCUMENTS

| | | | | |
|---|---|---|---|---|
| 6,337,992 | B1* | 1/2002 | Gelman | A61B 6/032 128/899 |
| 6,463,121 | B1* | 10/2002 | Milnes | A61B 6/4482 378/62 |
| 6,628,981 | B2* | 9/2003 | Baker | A61B 6/032 378/8 |
| 6,745,066 | B1 | 6/2004 | Lin et al. | |
| 6,763,082 | B2* | 7/2004 | Ozaki | A61B 6/032 378/15 |
| 6,968,225 | B2 | 11/2005 | Vu | |
| 7,269,246 | B2* | 9/2007 | Ohishi | A61B 6/481 378/196 |
| 7,277,524 | B2* | 10/2007 | Bruder | A61B 6/032 378/15 |
| 7,313,216 | B2* | 12/2007 | Nishide | A61B 6/032 378/15 |
| 7,403,587 | B2* | 7/2008 | Bontus | A61B 6/032 378/15 |
| 7,406,148 | B2* | 7/2008 | Russinger | A61B 6/504 378/15 |
| 7,421,100 | B2* | 9/2008 | Truyen | G06T 11/00 345/581 |
| 7,606,614 | B2* | 10/2009 | Licato | A61B 6/481 378/66 |
| 7,756,242 | B2* | 7/2010 | Kudo | A61B 6/032 378/15 |
| 7,805,181 | B2* | 9/2010 | Breeuwer | A61B 5/055 382/128 |
| 7,822,171 | B2* | 10/2010 | Bontus | G06T 11/005 378/11 |
| 7,831,011 | B2* | 11/2010 | Ayala | A61B 6/032 378/15 |
| 7,840,255 | B2* | 11/2010 | Ichihara | A61B 6/481 600/407 |
| 7,853,309 | B2* | 12/2010 | Ichihara | A61B 6/481 600/407 |
| 7,974,682 | B2* | 7/2011 | Gonzalez Molezzi | A61B 6/481 600/413 |
| 7,978,810 | B2* | 7/2011 | Schwarz | A61B 6/027 378/19 |
| 8,086,001 | B2* | 12/2011 | Bredno | A61B 6/032 382/128 |
| 8,111,891 | B2* | 2/2012 | Ichihara | A61B 5/0275 378/4 |
| 8,126,109 | B2* | 2/2012 | Tsukagoshi | A61B 6/032 378/51 |
| 8,155,466 | B2* | 4/2012 | Licato | G06T 5/10 358/3.26 |
| 8,160,338 | B2* | 4/2012 | Ichihara | A61B 6/481 378/4 |
| 8,229,547 | B2* | 7/2012 | Rauscher-Scheibe | A61B 6/032 382/128 |
| 8,265,224 | B2* | 9/2012 | Baumgart | A61B 6/12 378/114 |
| 8,280,492 | B2* | 10/2012 | Niethammer | A61B 6/032 378/4 |
| 8,315,449 | B2* | 11/2012 | Kemper | G06K 9/6223 382/128 |
| 8,428,694 | B2* | 4/2013 | Kalafut | A61B 6/507 382/128 |
| 8,483,799 | B2* | 7/2013 | Böing | A61B 6/032 378/15 |
| 8,509,507 | B2* | 8/2013 | Meetz | G06T 7/0012 128/922 |
| 8,615,116 | B2* | 12/2013 | Lardo | A61B 6/032 378/4 |
| 8,633,945 | B2* | 1/2014 | Nakamura | A61B 6/52 345/629 |
| 8,655,432 | B2* | 2/2014 | Hempel | A61B 6/481 600/407 |
| 8,682,051 | B2 | 3/2014 | Imas et al. | |
| 8,792,616 | B2* | 7/2014 | Tanaka | A61B 6/0457 378/20 |
| 8,825,139 | B2* | 9/2014 | Bernhardt | A61B 6/481 600/431 |
| 8,908,939 | B2* | 12/2014 | Bredno | A61B 6/481 382/128 |
| 8,965,080 | B2* | 2/2015 | Meetz | A61B 6/032 382/128 |
| 8,965,085 | B2* | 2/2015 | Sakaguchi | A61B 6/481 382/128 |
| 9,050,055 | B2* | 6/2015 | Korporaal | A61B 6/481 |
| 9,055,919 | B2* | 6/2015 | Proksa | A61B 5/4869 |
| 9,082,211 | B2* | 7/2015 | Prevrhal | G06T 11/005 |
| 9,089,308 | B2* | 7/2015 | Canstein | A61B 6/481 |
| 9,194,821 | B2* | 11/2015 | Sakai | G01N 23/046 |
| 9,198,625 | B2* | 12/2015 | Tsukagoshi | A61B 6/032 |
| 9,235,907 | B2* | 1/2016 | Ramirez Giraldo | G06T 11/003 |
| 9,271,656 | B2* | 3/2016 | Korporaal | A61B 5/026 |
| 9,307,947 | B2* | 4/2016 | Taguchi | A61B 6/481 |
| 9,317,915 | B2* | 4/2016 | Boese | G06T 11/003 |
| 9,332,946 | B2* | 5/2016 | Heuscher | A61B 6/032 |
| 9,406,146 | B2* | 8/2016 | Wiemker | G06T 7/20 |
| 9,414,751 | B2* | 8/2016 | Ichihara | A61B 6/481 |
| 9,433,392 | B2* | 9/2016 | Ohishi | A61B 6/463 |
| 9,460,509 | B2* | 10/2016 | Funabasama | A61B 6/032 |
| 9,582,152 | B2* | 2/2017 | Gulaka | G16H 40/63 |
| 9,595,101 | B2* | 3/2017 | Kato | G06T 11/005 |
| 9,597,042 | B2* | 3/2017 | Proksa | A61B 6/032 |
| 9,597,051 | B2* | 3/2017 | Gatayama | A61B 6/469 |
| 9,600,883 | B2* | 3/2017 | Carlsen | G01R 33/56366 |
| 9,616,166 | B2* | 4/2017 | Kalafut | A61M 5/007 |
| 9,649,041 | B2* | 5/2017 | Ohyu | A61B 5/0263 |
| 9,691,148 | B2* | 6/2017 | Fujisawa | A61B 6/481 |
| 9,734,578 | B2* | 8/2017 | Ohyu | A61B 6/481 |
| 9,757,083 | B2* | 9/2017 | Meetz | A61B 6/501 |
| 9,905,001 | B2* | 2/2018 | Ikeda | A61B 6/032 |
| 9,907,525 | B2* | 3/2018 | Ohishi | A61B 6/5217 |
| 9,907,529 | B2* | 3/2018 | Flohr | A61B 6/484 |
| 9,955,934 | B2* | 5/2018 | Vembar | A61B 6/481 |
| 10,010,305 | B2* | 7/2018 | Tsuyuki | A61B 6/56 |
| 10,159,454 | B2* | 12/2018 | Grant | A61B 6/481 |
| 2008/0119715 | A1 | 5/2008 | Gonzalez Molezzi et al. | |
| 2009/0022268 | A1 | 1/2009 | Kudo | |
| 2009/0202035 | A1 | 8/2009 | Tsukagoshi | |
| 2010/0290686 | A1 | 11/2010 | Canstein et al. | |
| 2011/0170662 | A1 | 7/2011 | Baumgart | |
| 2013/0343512 | A1 | 12/2013 | Heuscher et al. | |

FOREIGN PATENT DOCUMENTS

| | | |
|---|---|---|
| WO | 9917809 A2 | 4/1999 |
| WO | 2014036638 A1 | 3/2014 |

OTHER PUBLICATIONS

Morhard D et al: "Optimal Sequence Timing of CT Angiography and Perfusion CT in Patients with Stroke", European Journal of Radiology, Elsevier Science, NL, vol. 82, No. 6, Feb. 8, 2013; pp. e286-e289.

Allmendinger, A. et al., "Imaging of Stroke: Part I, Perfusion CT—Overview of Imaging Technique, Interpretation Pearls, and Common Pitfalls," American Journal of Roentgenology, vol. 198, No. 1, Jan. 2012, 11 pages.

(56) References Cited

OTHER PUBLICATIONS

Menon, B. et al., "Multiphase CT Angiography: A New Tool for the Imaging Triage of Patients with Acute Ischemic Stroke," Radiology, vol. 275, No. 2, May 2015, Available Online Jan. 29, 2015, 11 pages.
Jackson, John Irvin et al., "Methods and Systems for Adaptive Scan Control," U.S. Appl. No. 15/004,155, filed Jan. 22, 2016, 37 pages.

* cited by examiner

METHODS AND SYSTEMS FOR ADAPTIVE SCAN CONTROL

FIELD

Embodiments of the subject matter disclosed herein relate to non-invasive diagnostic imaging, and more particularly, to real-time adaptive scanning.

BACKGROUND

Non-invasive imaging technologies allow images of the internal structures of a patient or object to be obtained without performing an invasive procedure on the patient or object. In particular, technologies such as computed tomography (CT) use various physical principals, such as the differential transmission of x-rays through the target volume, to acquire image data and to construct tomographic images (e.g., three-dimensional representations of the interior of the human body or of other imaged structures).

For emergency room (ER) stroke management, time is critical to determine a proper course of treatment. For every minute a large vessel ischemic stroke is untreated, the average patient loses 1.9 million neurons. For each hour in which a treatment fails, the patient loses as many neurons as it does in almost 3.6 years of normal aging. Current standards of care require two contrast boli for separate CT angiography (CTA) and CT perfusion (CTP) studies. Further, prior to performing CTA and CTP studies, typical methods first perform a timing bolus scan, wherein a small contrast bolus is administered to a patient and subsequent contrast levels within the patient are monitored to generate a CTP/CTA scan plan personalized to the patient. However, the timing bolus scan alone takes five minutes, and performing CTA and CTP studies separately requires five to seven minutes between acquisitions to allow contrast washout.

BRIEF DESCRIPTION

In one embodiment, a method comprises: while performing a scan of a scan subject, processing acquired projection data to measure a contrast level; responsive to the contrast level increasing above a first threshold, automatically switching the scan from a first scan protocol to a second scan protocol; responsive to the contrast level decreasing below a second threshold, automatically switching the scan from the second scan protocol to the first scan protocol; and responsive to the contrast level decreasing below a third threshold, automatically ending the scan. In this way, multiple scan protocols, such as angiography and perfusion scan protocols, can be interleaved within a single scan. Furthermore, perfusion studies can be carried out without performing a contrast bolus timing scan. As a result, the radiation dose, contrast dose, and time of ischemic stroke assessment is substantially reduced.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 6:
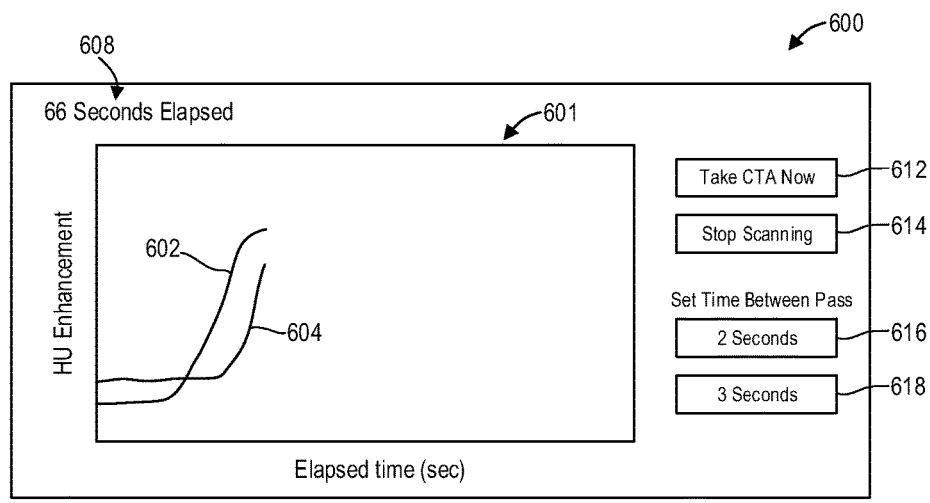
FIG. 6 shows an example user interface for monitoring contrast enhancement according to an embodiment of the invention.
Figure 7:
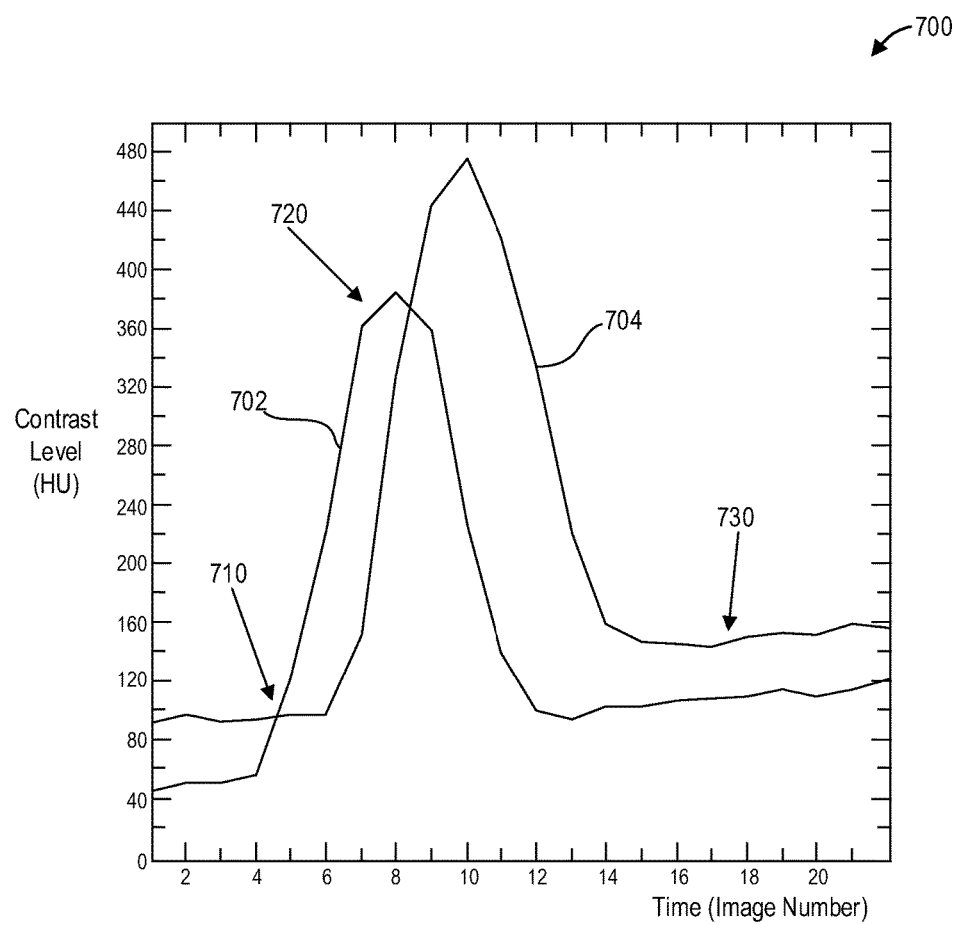
FIG. 7 shows a graph illustrating example contrast enhancement curves generated during a scan and used to adaptively control the scan according to an embodiment of the invention.

The following description relates to various embodiments of medical imaging systems. In particular, methods and systems are provided for adaptively controlling a diagnostic scan by monitoring contrast enhancement. An example of a computed tomography (CT) imaging system that may be used to acquire images processed in accordance with the present techniques is provided in FIGS. 1 and 2. A method for adaptive scan control, such as the method shown in FIG. 3, may include monitoring contrast levels during a scan and adjusting scan parameters responsive thereto. Such a method enables personalization of scan protocols on a patient-by-patient basis. Furthermore, by adapting scans based on monitored contrast levels in real-time, multiple scan protocols may be combined into a single scan. As an example, a method, such as the method depicted in FIGS. 4 and 5, includes interleaving CT angiography (CTA) and CT perfusion (CTP) scans into a single scan by switching scan protocols responsive to contrast levels measured during the scan. An operator of the CT imaging system may manually intervene in the automatic adjustment of scan parameters via a user interface such as that shown in FIG. 6. Transitions between different stages of a multi-protocol scan may be triggered based on levels and slopes of multiple contrast curves, including arterial and venous curves, as depicted in FIG. 7.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality.

As used herein, the phrase "pixel" also includes embodiments of the invention where the data is represented by a "voxel." Thus, both the terms "pixel" and "voxel" may be used interchangeably herein.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

Various embodiments may be implemented in connection with different types of imaging systems. For example, various embodiments may be implemented in connection with a CT imaging system in which an x-ray source projects a fan- or cone-shaped beam that is collimated to lie within an x-y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third-generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector. Further, "short scan" images may also be reconstructed from a set of views acquired over less than a full gantry rotation.

In an axial scan, the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on, for example, a cathode ray tube display.

Figure 1:
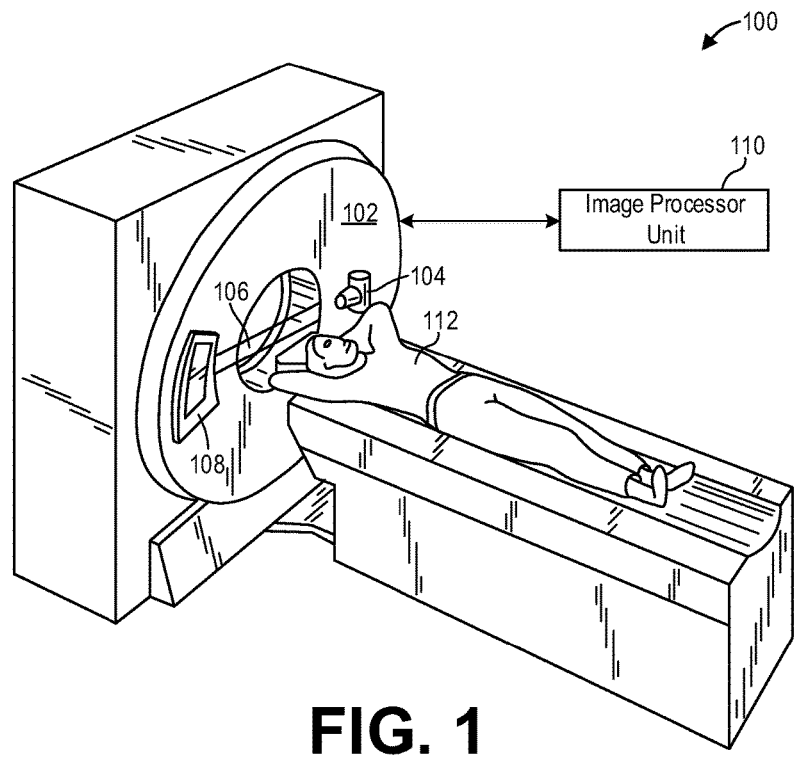
FIG. 1 shows a pictorial view of an imaging system according to an embodiment of the invention.

FIG. 1 illustrates an exemplary CT system 100 configured to allow fast and iterative image reconstruction. Particularly, the CT system 100 is configured to image a subject such as a patient 112, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104, also generally referred to herein as radiation source 104, configured to project a beam of x-ray radiation 106 for use in imaging the patient 112. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources may be employed to project a plurality of x-rays 106 for acquiring projection data corresponding to the patient at different energy levels.

In certain embodiments, the CT system 100 further includes an image processor unit 110, also referred to herein as image processing unit 110, configured to reconstruct images of a target volume of the patient using an iterative or analytic image reconstruction method. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

Figure 2:
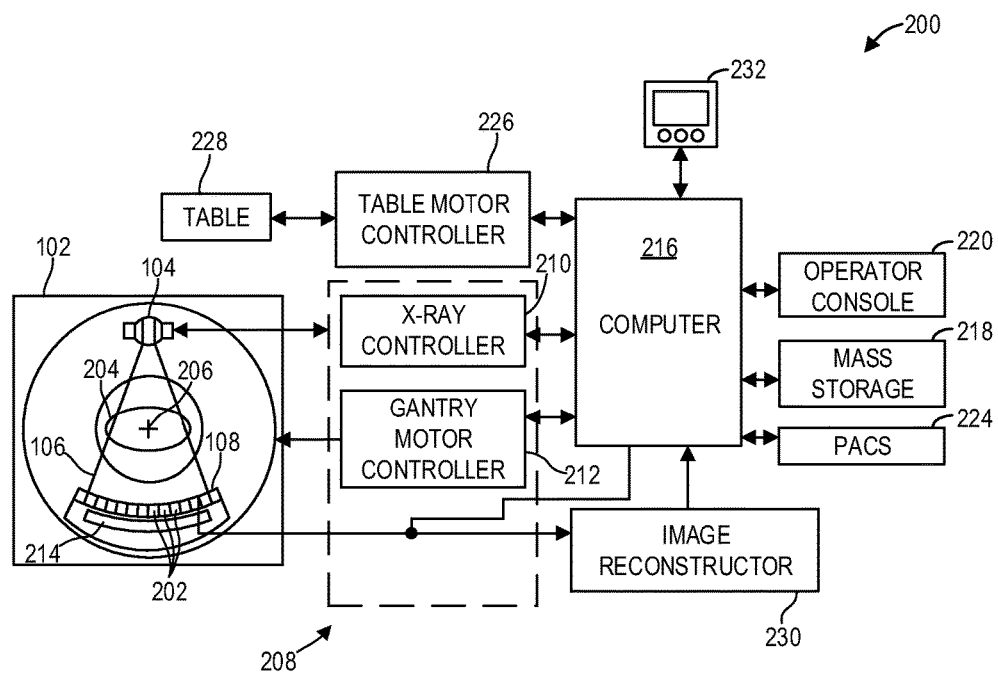
FIG. 2 shows a block schematic diagram of an exemplary imaging system according to an embodiment of the invention.

FIG. 2 illustrates an exemplary imaging system 200 similar to the CT system 100 of FIG. 1. In accordance with aspects of the present disclosure, the imaging system 200 is configured to reconstruct images with a user-specified temporal window in real-time. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer 216, also referred to herein as computing device 216. In one example, the computer 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computer 216 provides commands and parameters to one or more of the DAS 214, the x-ray controller 210, and the gantry motor controller 212 for controlling system operations such as data acquisition and/or processing. In certain embodiments, the computer 216 controls system operations based on operator input. The computer 216 receives the operator input, for example, including commands and/or scanning parameters via an operator console 220 operatively coupled to the computer 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computer 216 uses the operator-supplied and/or system-defined commands and parameters to operate a table motor controller 226, which in turn, may control a motorized table 228. Particularly, the table motor controller 226 moves the motorized table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computer 216 for generating useful patient information for diagnosis and evaluation. In certain embodiments, the computer 216 transmits the reconstructed images and/or the patient information to a display 232 communicatively coupled to the computer 216 and/or the image reconstructor 230.

The various methods and processes described further herein may be stored as executable instructions in non-transitory memory on a computer 216 in imaging system 200. In one embodiment, image reconstructor 230 may include such instructions in non-transitory memory, and may apply the methods described herein to reconstruct an image from scanning data. In another embodiment, computer 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computer 216.

In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

Figure 3:
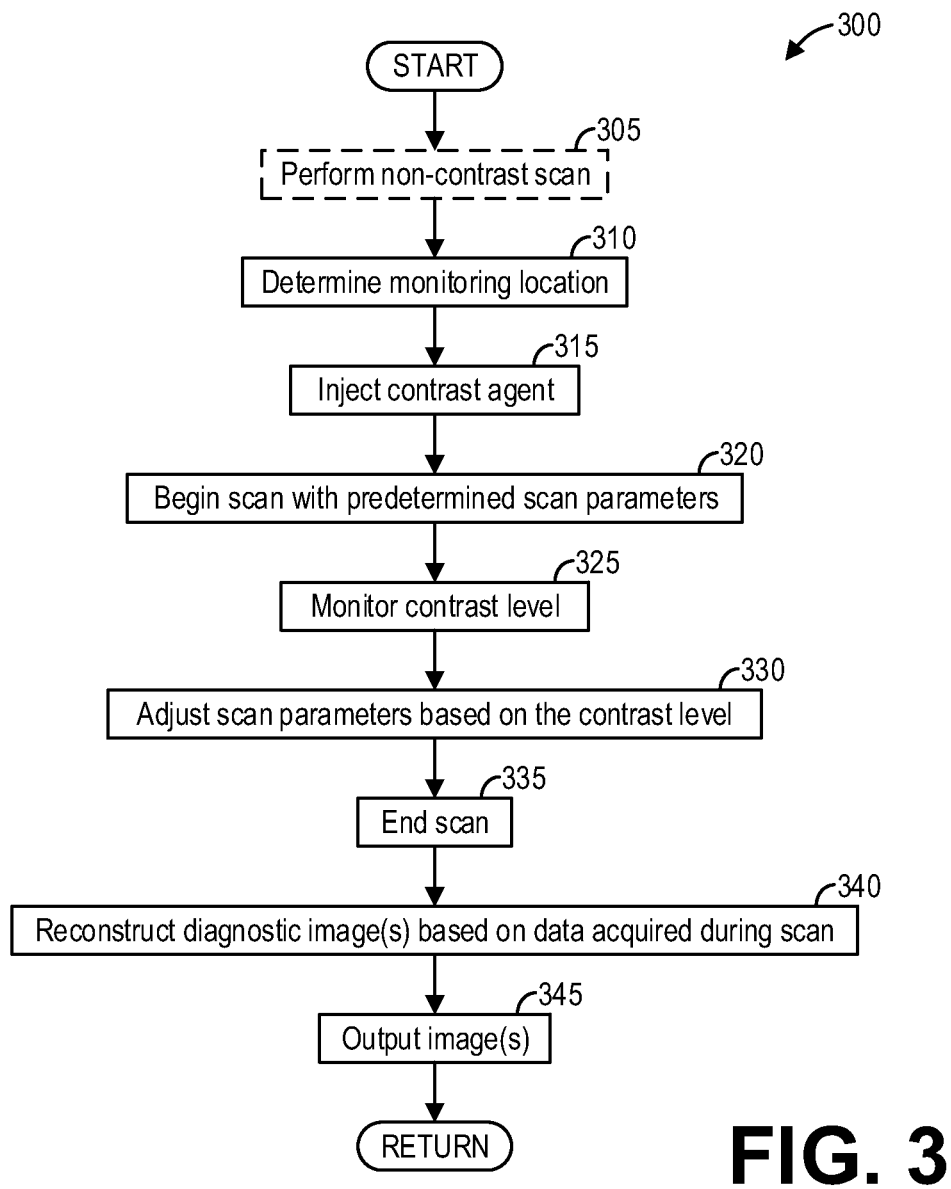
FIG. 3 shows a high-level flow chart illustrating an example method for adaptive scanning with contrast monitoring according to an embodiment of the invention.

FIG. 3 shows a high-level flow chart illustrating an example method 300 for updating a scan plan in real time according to an embodiment. In particular, method 300 relates to, during a scan, monitoring the scan and updating scan parameters. Method 300 may be carried out by the components and systems depicted in FIGS. 1 and 2, however it should be understood that the method may be implemented on other components and systems not depicted without departing from the scope of the present disclosure.

Method 300 may begin at 305. At 305, method 300 may optionally include performing a non-contrast scan. The non-contrast scan may be taken to establish a baseline image for the area to be monitored before delivery of a contrast agent. The baseline image may then be used to align the patient and the region of interest within the imaging device.

At 310, method 300 includes determining a monitoring location. The monitoring location comprises a specific region of the patient wherein contrast level is monitored during the scan. Furthermore, the monitoring location may be positioned within the imaging area such that the projection data acquired for diagnostic purposes may also be used for monitoring. Thus, an operator may select the monitoring location based on the baseline image acquired at 305. Determining the monitoring location may therefore comprise receiving a selection of a monitoring location from an operator, for example via operator console 220.

At 315, method 300 includes injecting a contrast agent into the patient. As a non-limiting example, the contrast agent may comprise iodine. As other examples, the contrast agent may comprise an ionic contrast medium such as meglucamine diatriozoate, or a non-ionic contrast medium such as iopromide or ohexol. The contrast agent may be intravenously injected using either automatic or manual methods.

At 320, method 300 includes beginning a scan with predetermined scan parameters. Scan parameters may include, but are not limited to, slice thickness, reconstruction interval, pitch, table speed, scan delay, and so on. The scan parameters may be predetermined according to various methods. For example, an operator may manually set the scan parameters based on experience. As another example, a prediction model may automatically determine the scan parameters based on, for example, the anatomical part being imaged and patient-specific data. The scan parameters may further be determined based on contrast administration, including but not limited to iodine concentration of the contrast agent, injection flow rate (e.g., amount of contrast delivered per unit time), injection duration (e.g., contrast volume), and so on.

At 325, method 300 includes monitoring a contrast level. Specifically, method 300 monitors the contrast level at the monitoring region selected at 310. As an example, monitoring the contrast level comprises evaluating the difference, over time, between an HU value at the monitoring region and a baseline value at the monitoring region. The baseline value may be obtained, as a non-limiting example, from the non-contrast scan optionally obtained at 305, or may be obtained from the beginning of the scan (e.g., before the contrast agent perfuses to the monitoring region). The evaluated difference between the HU value and the baseline value at the monitoring region may be displayed to an operator as a contrast enhancement curve, which comprises a plot of the difference over time. Example contrast enhancement curves are described further herein with regard to FIGS. 5-6.

In some examples, monitoring the contrast level further includes evaluating rate of change in contrast level (e.g., an instantaneous rate of change or the slope of the contrast enhancement curve). For example, a positive rate of change indicates that the contrast level is increasing, while a negative rate of change indicates that the contrast level is decreasing.

Method 300 monitors the contrast level throughout the duration of the scan. Meanwhile, at 330, method 300 includes adjusting scan parameters based at least on the contrast level. Scan parameters may include, but are not limited to, dose (i.e., tube current levels, tube peak kilovoltage), table position, scan region, temporal sampling rate or scan delay (i.e., time between successive acquisitions during the scan), and so on. Adjusting such scan parameters responsive to the contrast level may comprise automatically adjusting one or more scan parameters responsive to contrast level thresholds. Further, an operator of the imaging apparatus may override one or more automatic triggers (i.e., actions performed responsive to contrast level thresholds) by manually adjusting scan parameters during the scan.

In this way, method 300 monitors the contrast level and adaptively controls the scan based on the contrast level. For the purposes of this disclosure, the term "real time" is defined to include a procedure that is performed without any intentional delay. For example, an embodiment may acquire images of the monitoring region and evaluate the contrast level in the acquired images at a real-time rate of, as a non-limiting example, ten volumes per second. However, it should be understood that the real-time rate may be dependent on the time that it takes to acquire and process each volume of data. Accordingly, when acquiring a relatively large volume of data, the real-time rate may be slower. Thus, some embodiments may have real-time rates that are considerably faster than ten volumes per second, while other embodiments may have real-time rates slower than ten volumes per second.

Adjusting the scan parameters at 330 responsive to measured contrast levels enables the method to interleave multiple scan protocols into a single scan. For example, as described further herein with regard to FIG. 4, the method may switch from a CT perfusion scan protocol to a CT angiography scan protocol at peak contrast enhancement, and then switch back to the CT perfusion scan protocol. Further, the method may adapt the multiple protocols based on the measured contrast level (and hence, based on the particular patient being scanned). Further still, additional scan protocols such as multi-phase angiography may be performed alongside other scan protocols. For example, multi-phase angiography scan protocols may include a standard angiography acquisition during peak contrast enhancement, and may further include additional angiography acquisitions during mid- and late-venous phases. Such additional angiography acquisitions may be performed according to scan protocols appropriate to the later phases; for example, the additional angiography acquisitions may use different dose and/or scan regions and/or temporal sampling rates with respect to the CTA acquisition performed during peak contrast enhancement. Thus, the method may switch between CTP and CTA protocols multiple times during a single scan, wherein the scan parameters for both the CTP and the CTA acquisitions may be adapted throughout. It should also be appreciated that scan protocols other than CTA and CTP may be interleaved during a single scan.

The scan ends at 335. Proceeding to 340, method 300 includes reconstructing one or more diagnostic images based on data acquired during the scan. The one or more diagnostic images may be reconstructed using known reconstruction techniques, such as filtered backprojection or iterative reconstruction.

At 345, method 300 includes outputting the one or more diagnostic images. As non-limiting examples, outputting the one or more diagnostic images may comprise outputting the one or more diagnostic images to a display device (e.g., display device 232) for display to an operator or a physician, to a storage medium (e.g., mass storage 218) for retrieving at a later time, and so on. Method 300 may then end.

Thus, a method comprises, during a scan, acquiring projection data, processing said projection data to monitor contrast enhancement levels in real-time, and adjusting scan parameters based on the contrast enhancement levels. In this way, radiation dosage can be reduced by eliminating a separate and dedicated contrast monitor, and a scan protocol can be automatically adapted to a particular patient being scanned. Furthermore, the method enables interleaving of multiple scan protocols in a single scan, thus reducing scan time altogether. This benefit proves particularly advantageous in scenarios wherein the usage of time is critical. For example, in ischemic stroke assessment, CT angiography (CTA) and CT perfusion (CTP) exams are performed as part of the standard procedure. Time is especially critical for these exams because patients suffering from a stroke lose approximately two million neurons per minute. However, when the CTA is performed before the CTP, the total CT exam time is increased because a delay is inserted between the scans to avoid venous contamination. When the CTA is performed after the CTP, venous contamination in the CTA can affect decision accuracy. The methods described herein allow these exams to be combined seamlessly while avoiding venous contamination and optimizing CT exam time and dose. Specifically, as described further herein with regard to FIG. 4, a CT angiography (CTA) scan and a CT perfusion (CTP) scan can be interleaved by real-time monitoring and adapting.

Figure 4:
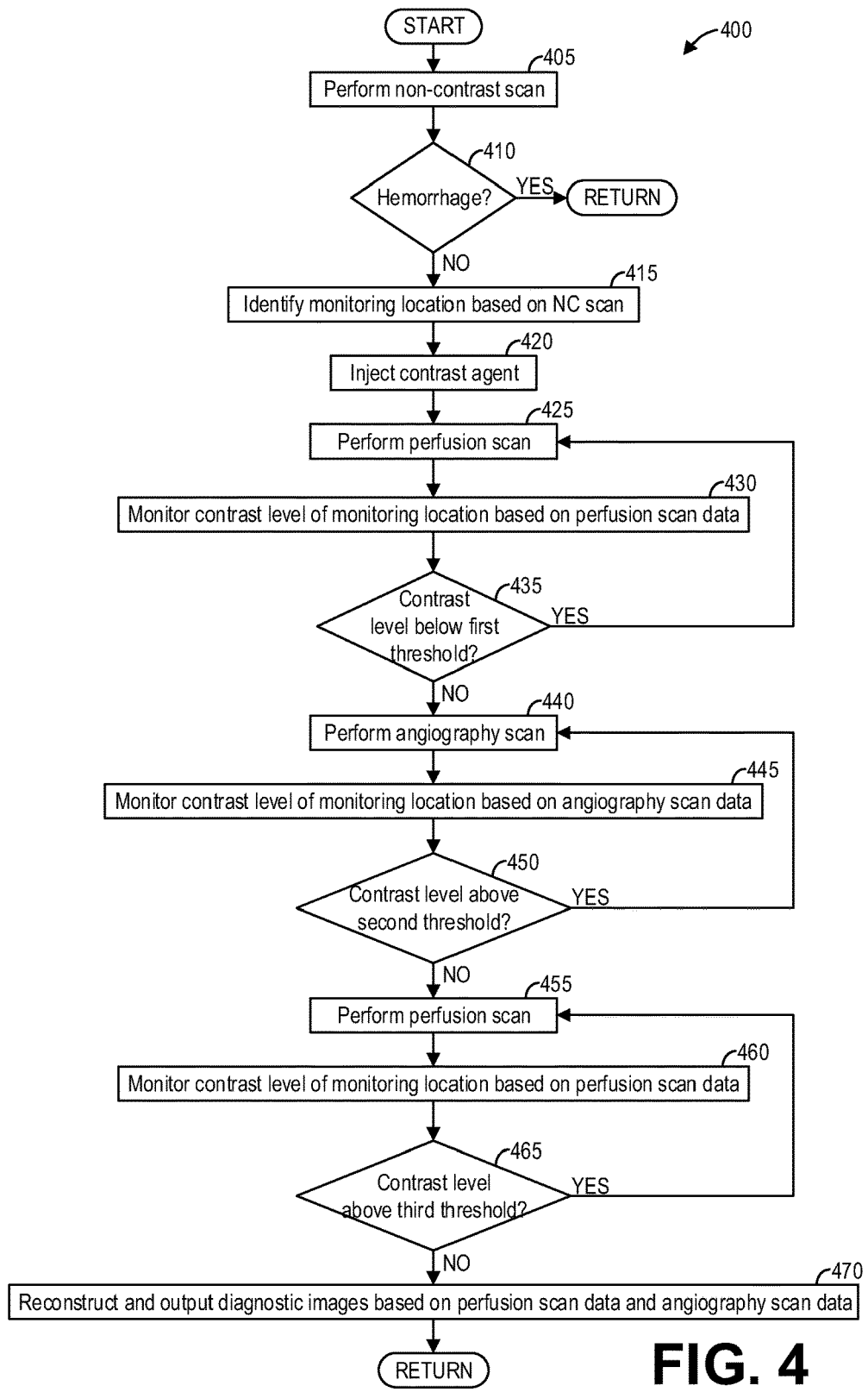
FIG. 4 shows a high-level flow chart illustrating an example method for adaptive scanning with interleaved imaging techniques according to an embodiment of the invention.

FIG. 4 shows a high-level flow chart illustrating an example method 400 for updating a scan plan in real-time according to an embodiment. In particular, method 400 relates to interleaving a perfusion scan and an angiography scan by monitoring a contrast level and adjusting scan parameters based on the monitored contrast level. Method 400 may be carried out by the components and systems depicted in FIGS. 1 and 2, however it should be understood that the method may be implemented on other components and systems not depicted without departing from the scope of the present disclosure.

Method 400 may begin at 405. At 405, method 400 includes performing a non-contrast scan of the target volume or region of interest (e.g., the head of the patient). Performing the non-contrast scan includes acquisition of projection data as well as the reconstruction of the acquired projection data into one or more images. The non-contrast scan enables a physician to rule out a brain aneurysm or a cerebral hemorrhage before proceeding to additional diagnostic scans.

Furthermore, by way of such a scan, images are acquired at positions in the scan range where there is no contrast agent. Thus, the non-contrast scan may comprise a baseline scan which establishes baseline contrast values (i.e., contrast levels prior to contrast injection) in a monitoring region.

After performing the non-contrast scan, method 400 continues to 410. At 410, method 400 includes assessing, based on the non-contrast scan, if a hemorrhage is occurring. In some examples, a physician may review images from the non-contrast scan to assess whether a hemorrhage has occurred. In other examples, the method may automatically evaluate images from the non-contrast scan to assess whether a hemorrhage has occurred, for example by using an atlas or previous scans of the patient.

If a hemorrhage has occurred ("YES"), the patient should be promptly treated rather than continuing to undergo diagnostic scans, and so method 400 promptly ends. However, if a hemorrhage has not occurred ("NO"), additional scanning may be performed to identify a suitable course of treatment. Method 400 proceeds to 415.

At 415, method 400 includes identifying one or more monitoring locations based on the non-contrast scan. In some examples, an operator of the CT system may select one or more monitoring locations based on the non-contrast scan.

At 420, method 400 includes injecting a contrast agent. The contrast agent may be manually or automatically intravenously injected into the patient. The contrast agent may be an imaging enhancing agent, a biomedical agent, a blood agent, a nonionic contrast agent, an iodinated contrast agent, and so on.

After injecting the contrast agent, method 400 proceeds to 425. At 425, method 400 includes performing a perfusion scan. Performing a perfusion scan comprises scanning the patient according to perfusion scan parameters, including but not limited to scan sampling interval and radiation dosage, in order to generate one or more perfusion maps and determine various perfusion parameters such as cerebral blood flow, cerebral blood volume, mean transit time, and so on. The scan sampling interval comprises an amount of time between scans, and may range from one to five seconds.

While method 400 performs the perfusion scan, the method also monitors contrast levels in real-time by processing the acquired projection data. Specifically, at 430, method 400 includes monitoring a contrast level of the monitoring location based on the perfusion scan data. Monitoring the contrast level of the monitoring location based on the perfusion scan data may comprise, as a non-limiting example, reconstructing an image of at least the monitoring location based on the perfusion scan data and evaluating the contrast or HU level of the image. In some examples, method 400 may reconstruct only one or two slices to monitor the contrast levels. However, in other examples, method 400 may reconstruct the full volume to monitor the contrast levels.

At 435, method 400 includes determining if the contrast level is below a first threshold. The first threshold is established such that above the first threshold, the contrast is reaching peak contrast enhancement. To that end, in some examples the first threshold may comprise a vector indicating a scalar amount of contrast as well as a direction indicating that the increase in contrast is reaching a maximum. Further, in some examples the method automatically determines whether the contrast level has reached the first threshold. Alternatively or additionally, an operator of the imaging apparatus may manually indicate, based on a review of the contrast curves, that the contrast enhancement is reaching a maximum by selecting a button via an operator console and/or a display device.

If the contrast level is below the first threshold ("YES"), then method 400 may return to 425 and continue performing the perfusion scan. If the contrast level is above the first threshold ("NO"), then method 400 proceeds to 440.

At 440, method 400 includes performing an angiography scan. An angiography scan is performed at peak contrast enhancement, which is why method 400 performs the angiography scan responsive to the contrast level above the first threshold. To perform the angiography scan, the method adjusts multiple scan parameters, including but not limited to dose, region of interest (e.g., head and neck instead of just the head), and so on.

At 445, method 400 includes monitoring the contrast level of the monitoring location based on the angiography scan data. Monitoring the contrast level of the monitoring location based on the angiography scan data may comprise, as a non-limiting example, reconstructing an image of at least the monitoring location based on the angiography scan data and evaluating the contrast or HU level of the image.

At 450, method 400 includes determining if the contrast level is above a second threshold. The second threshold is established such that when the contrast level reaches the second threshold, the contrast level is exiting peak contrast enhancement. To that end, in some examples the second threshold may comprise a vector indicating a scalar amount of contrast as well as a direction indicating that the contrast is decreasing away from peak contrast enhancement. Further, in some examples the method automatically determines whether the contrast level has reached the second threshold. Alternatively or additionally, an operator of the imaging apparatus may manually indicate that the contrast level is decreasing away from the maximum by selecting a button via an operator console and/or a display device.

If the contrast level is above the second threshold ("YES"), method 400 returns to 440 and performs another angiography scan and monitors the contrast level based on the acquired angiography scan data.

However, if the contrast level is below the second threshold ("NO"), method 400 proceeds to 455. At 455, method 400 includes performing a perfusion scan. To perform the perfusion scan, the method adjusts one or more scan parameters. Furthermore, the scan parameters may be different than the scan parameters used for the perfusion scan performed at 425. For example, the temporal sampling rate may be increased in comparison to the temporal sampling rate used at 425.

While performing the perfusion scan, the method continues to monitor the contrast levels. Specifically, at 460, method 400 includes monitoring the contrast level of the monitoring location based on the perfusion scan data.

At 465, method 400 includes determining if the contrast level is above a third threshold. The third threshold is established such that when the contrast level reaches the third threshold, the contrast is washed out (e.g., returned to baseline level). The third threshold may be selected based on the non-contrast scan, for example, or in some examples may be automatically selected based on contrast levels measured at the beginning of the perfusion scan.

If the contrast level is above the third threshold ("YES"), method 400 returns to 455 to continue performing the perfusion scan and monitoring the contrast levels based on the acquired perfusion scan data.

However, if the contrast level is below the third threshold ("NO"), method 400 proceeds to 470. At 470, scanning is complete and method 400 includes reconstructing and outputting diagnostic images based on the perfusion scan data and the angiography scan data as well as computing perfusion parameters. Method 400 may then end.

Thus, the system control can automatically adapt the scan parameters and contrast injection parameters based upon acquired image data, in combination with or as an alternative to adaptations based upon dynamic scan subject data. When a contrast agent is administered and a scan is commenced, image data will be acquired from the ROI. Based upon the image data acquired in real-time, the system can determine the present enhancement value of the contrast agent in the ROI and update or adapt such parameters as the flow rate or pressure of the injection process, x-ray tube current or voltage, x-ray dosage, pitch, gantry rotation, scan resolution, image data weighting, image acquisition trajectories, scan region, and the like, in real-time. Accordingly, if image data reveals that contrast enhancement has reached or will reach its peak enhancement value sooner or later than expected, the system can adjust scan and contrast parameters on the fly so that the image data acquisition, or a particular portion thereof, will still coincide with the time of maximum contrast enhancement. For example, in a CT scan, the system control could adjust the tube current and/or tube voltage in real time to scan a patient at a maximum dosage during the peak contrast enhancement, based upon enhancement calculations from acquired image data.

Figure 5:
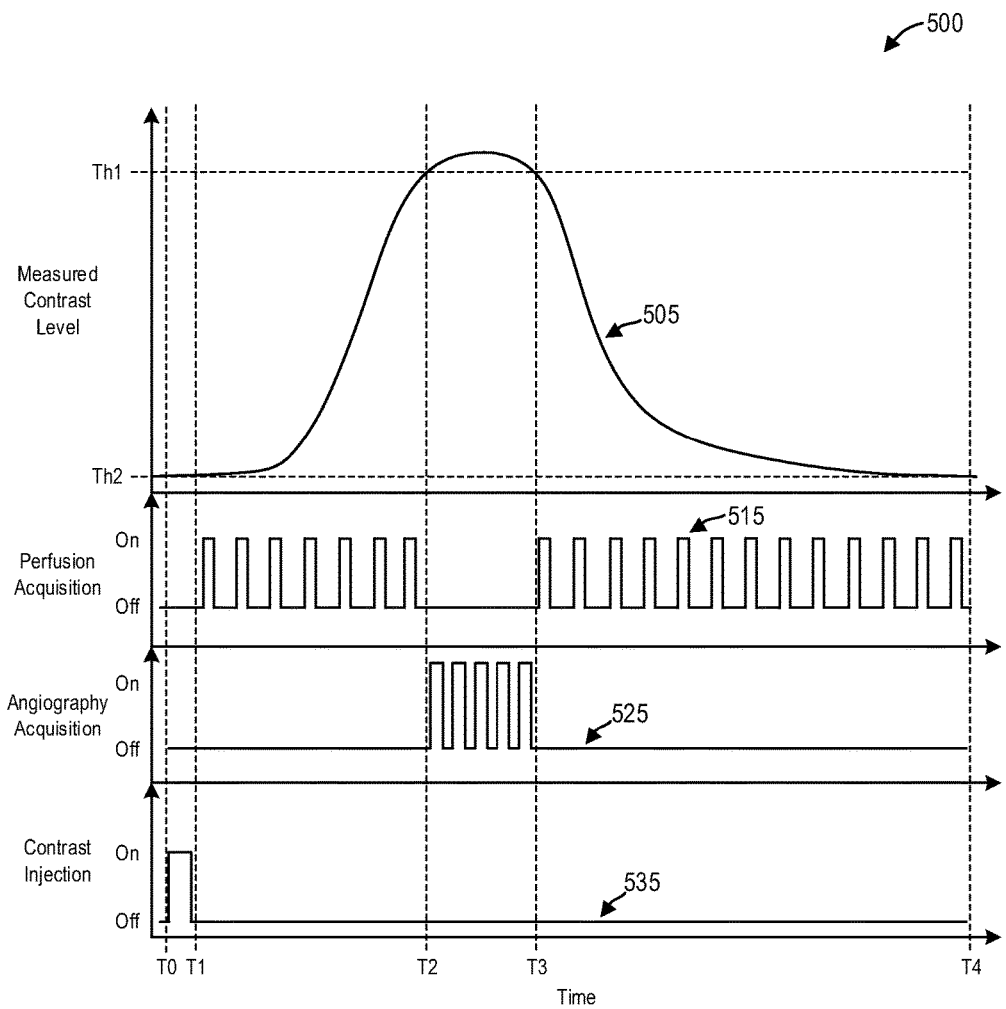
FIG. 5 shows a set of graphs illustrating an example control of an imaging system according to an embodiment of the invention.

FIG. 5 shows a set of graphs 500 illustrating example operating conditions during a scan performed in accordance with the method 400. The set of graphs includes a plot 505 of measure contrast level over time, a plot 515 of perfusion acquisition over time, a plot 525 of angiography acquisition over time, and a plot 535 of contrast injection over time.

At time T0, contrast is injected as shown by plot 535. Though the contrast injection as shown as a pulse lasting for a relatively short time, in some examples the contrast may be injected for a longer duration than that shown in by plot 535. At time T1 shortly after the contrast injection begins, the perfusion scan begins as shown by plot 515. The perfusion acquisition comprises a series of scans occurring at regular intervals while the measured contrast level increases. By periodically performing scans while the contrast perfuses through the patient (as illustrated by the measured contrast level in 505), the acquired perfusion data may be used to generate a perfusion map illustrating the perfusion of contrast through the patient.

At time T2, the measured contrast level as shown by plot 505 reaches the threshold Th1 which indicates that the measured contrast level is reaching peak contrast enhancement. Therefore, responsive to reaching the threshold Th1, the perfusion acquisition ends and the angiography acquisition begins, as shown respectively by plots 515 and 525.

Between times T2 and T3, the angiography acquisition occurs while the measured contrast level is at peak contrast enhancement. At time T3, the measured contrast level reaches a second threshold indicated by the threshold Th1. However, in contrast to the first threshold at Th1, the slope of the measured contrast level is negative rather than positive, thereby indicating that the measured contrast level is decreasing away from the peak contrast enhancement. As a result, at time T3 the angiography acquisition ends and the perfusion acquisition begins. Switching from the angiography acquisition to the perfusion acquisition comprises adjusting one or more scan parameters. Furthermore, after time T3, the perfusion acquisition may include a different temporal sampling rate than the perfusion acquisition between times T1 and T2. As a non-limiting example, the temporal sampling rate may comprise 2 to 3 seconds between times T1 and T2, and the temporal sampling rate may comprise five or more seconds after time T3.

After the peak contrast enhancement, the measured contrast level decreases. At time T4, the measured contrast level reaches a third threshold indicated by threshold Th2. In some examples, the threshold Th2 may comprise the contrast level measured prior to the contrast injection at time T0. Responsive to the measured contrast level reaching the threshold Th2, the perfusion acquisition ends at time T4.

As described above, in some examples the contrast levels and the rate of change of the contrast levels may be used to automatically trigger the adjustment of scan parameters. For example, an example auto-trigger condition for switching from CTP to CTA may comprise:

If: $t > C0$, $AIF(t) > C1$, $\dfrac{AIF'(t)}{AIF'(t-1)} > C2$, and $AIF''(t) < 0$, Then: trigger "Take CTA Now"

where t represents time (set to zero at the beginning of the scan), AIF(t) is the instantaneous HU value of the arterial input function (AIF) at time t, AIF'(t) is the first derivative of the AIF at time t, AIF"(t) is the second derivative of the AIF at time t, and C0, C1, and C2 are hurdle values which may comprise constants or variables. The arterial input function (AIF) is a function calculated from a temporal change in the concentration of a contrast agent in an artery of the subject's tomographic image.

As another example, an example auto-trigger condition for adjusting the TSR after the arterial peak may comprise:

If: $t > C3$, $AIF''(t) < 0$, $AIF(t) < \max(AIF)$, $V''(t) < 0$, and $V(t) < \max(V)$, Then: adjust TSR to 5 seconds where V(t) is the instantaneous HU value of the venous curve at time t, V"(t) is the second derivative of the venous curve at time t, the function max(x) comprises the maximum measured value of a function x, and C3 is a hurdle or threshold value which may comprise a constant or a variable.

Thus, auto-trigger conditions for adapting scan parameters and protocols responsive to contrast levels measured in real time may additionally rely on factors such as instantaneous speed and acceleration of contrast level changes. Furthermore, the auto-trigger conditions may rely on multiple contrast curves, rather than a single contrast curve. The example auto-trigger conditions described above may be implemented as executable instructions in non-transitory memory in a controller, such as computer 216. It should be appreciated that the controller may include a plurality of additional auto-trigger conditions similar to those described above for automatically adjusting scan parameters responsive to contrast levels monitored in real time.

In some examples, the systems described herein may enable an operator of the system to manually intervene in the adaptive scan process. FIG. 6 shows an example user interface 600 for real-time contrast monitoring. User interface 600 may be displayed via a display device, such as display device 232. An operator may interact with the user interface 600 via an operator console, such as operator console 220, or via a touch screen device of the display device.

The user interface 600 may include a graph 601 which illustrates plots of measured contrast levels as a function of time. In particular, the graph 601 may include a plot 602 of arterial contrast level and a plot 604 of venous contrast level. The user interface 600 may further include a timer 608 indicating an amount of time elapsed since the beginning of the scan.

The user interface 600 may include one or more control buttons that allow an operator to adjust scan parameters. For example, the "Take CTA Now" button 612, when selected by the operator, switches the scan protocol from a perfusion protocol to a computed tomography angiography (CTA) protocol. The operator may select the "Take CTA Now" button 612 if the contrast curves 602 and/or 604 indicate peak contrast enhancement, in lieu of the system automatically detecting peak contrast enhancement or if the operator decides to initiate the CTA protocol prior to the system automatically switching to the CTA protocol.

As another example of a control button that allows an operator to adjust scan parameters, the user interface 600 may further include a "Stop Scanning" button 614 which, when selected by the operator, ends the scan.

As yet another example of a control button, the user interface 600 may include user inputs that allow an operator to adjust the temporal sampling rate of the perfusion scan. For example, the user interface 600 may be able to set the time between each pass using a "2 Seconds" button 616 or a "3 seconds" button 618, which respectively change the temporal sampling rate to two seconds or three seconds. In some examples, other temporal sampling rates may be offered, such as five seconds. In yet other examples, the user interface 600 may include a user input that allows the operator to manually input a temporal sampling rate.

Thus systems and methods are provided to enable an operator of the CT system to manually intervene in the automatic monitoring of contrast levels and adjusting of scan parameters in real-time during a scan. Multiple contrast curves may be monitored, including but not limited to arterial and venous contrast curves.

In some examples, transition time points (i.e., when to switch scan parameters) may be updated in real-time during a scan based on the monitored contrast levels and analysis of arterial and venous contrast uptake/washout curves. In this way, the scan protocol can be optimized for a particular patient.

FIG. 7 shows a graph 700 illustrating example contrast enhancement curves generated during a scan and used to adaptively control the scan according to an embodiment of the invention. In particular, the graph 700 illustrates example behavior of an arterial contrast curve 702 and a venous contrast curve 704, which respectively illustrate contrast levels of arterial blood and venous blood over time (measured in terms of image number, wherein the image number refers to images reconstructed from projection data of successive acquisitions during a scan). The contrast curves 702 and 704 are example contrast curves which may be generated, for example, during a scan carried out in accordance with the method of FIG. 4.

A scan may begin with a pre-defined scan plan comprising a plurality of stages, wherein each stage corresponds to a particular dose, scan range, scan-to-scan time, maximum number of exposures, a transition time point, and criteria for advancing or delaying the transition time point. For example, the initial perfusion scan may comprise several stages, wherein each stage comprises a different scan-to-scan time and a maximum number of exposures. The scan-to-scan time (or temporal sampling rate) may decrease from stage to stage as the contrast level increases, and the pre-defined scan plan may establish a transition time point (wherein the scan protocol transitions to the next stage) every five seconds during the CTP acquisition.

For example, the pre-determined scan plan may include a first stage wherein the dose is a CTP dose, the scan range is the head, the scan-to-scan time is three seconds, and the maximum number of exposures is twenty, and the scan plan may further include a second stage wherein the dose is a CTP dose, the scan range is the head, the scan-to-scan time is two seconds, and the maximum number of exposures is thirty. The pre-defined scan plan may include a transition time point of, say, ten seconds (measured from the beginning of the scan) for the scan to transition from the first stage to the second stage, and this transition time point may be selected based on, for example, statistical data of other patients' measured contrast curves.

As described above, auto-trigger conditions such as contrast curve level and slope may be used to override the pre-defined transition time points. For example, the scan protocol may switch from stage one to stage two at transition point 710, established by at least the contrast level and slope of the arterial curve 702.

The pre-defined scan plan may include a third stage wherein the dose is a CTA dose and/or the scan range is the neck and head and/or the scan-to-scan time is two seconds, and the maximum number of exposures is one. The scan protocol may automatically switch from the first stage to the second stage when the contrast level and slope of the arterial curve 702 reaches the transition point 720.

Additionally or alternatively, the auto-trigger conditions may be based on the level and slope of the venous curve 704. For example, the pre-defined scan plan may include a final stage wherein the TSR transitions from five seconds to fifteen seconds. The scan protocol may transition to this final stage when the venous curve reaches the level and slope indicated at transition point 730.

A technical effect of the disclosure is the interleaving of multiple scan protocols within a single dynamic scan session. Another technical effect of the disclosure is the reduction of time for ischemic stroke diagnosis imaging. Yet another technical effect of the disclosure is the performance of perfusion and angiography exams without the use of a separate contrast bolus timing scan. Another technical effect of the disclosure is the adjustment of one or more scan parameters, including a scan region, during a single scan. Another technical effect of the disclosure is the adaptation of a pre-defined scan plan in real-time during a scan.

Various systems and methods for dynamically adapting an imaging scan are provided. In one embodiment, a method comprises: while performing a scan of a scan subject, processing acquired projection data to measure a contrast level; responsive to the contrast level increasing above a first threshold, automatically switching the scan from a first scan protocol to a second scan protocol; responsive to the contrast level decreasing below a second threshold, automatically switching the scan from the second scan protocol to the first scan protocol; and responsive to the contrast level decreasing below a third threshold, automatically ending the scan.

In a first example of the method, the first scan protocol includes a first scan region of the scan subject, and the second scan protocol includes a second scan region of the scan subject, the second scan region larger than the first scan region. In a second example of the method optionally including the first example, the first scan region includes a head of the scan subject and the second scan region includes the head and a neck of the scan subject. In a third example of the method optionally including one or more of the first and the second examples, the method further comprises adjusting a temporal sampling rate of the first scan protocol responsive to the contrast level. In a fourth example of the method optionally including one or more of the first through third examples, processing the acquired projection data comprises reconstructing at least one image slice based on the acquired projection data. In a fifth example of the method optionally including one or more of the first through fourth examples, the first, second, and third thresholds comprise a threshold contrast level and a threshold rate of change of the contrast level. In a sixth example of the method optionally including one or more of the first through fifth examples, the first, second, and third thresholds are calculated based on a non-contrast scan performed prior to the scan. In a seventh example of the method optionally including one or more of the first through sixth examples, a contrast bolus timing scan is not performed prior to the scan. In an eighth example of the method optionally including one or more of the first through seventh examples, the method further comprises adjusting transition time points of the scan responsive to the contrast level. In a ninth example of the method optionally including one or more of the first through eighth examples, the contrast level is separately measured in an artery and a vein positioned within the first scan region. In a tenth example of the method optionally including one or more of the first through ninth examples, the method further comprises switching between the first and second scan protocols responsive to user input regardless of the contrast level.

In another embodiment, a non-transitory computer-readable storage medium includes executable instructions stored thereon that when executed by a computer cause the computer to: identify a monitoring location of a patient; administer a contrast agent to the patient; perform a single dynamic scan session to acquire image data, wherein during the single dynamic scan session, the instructions further cause the computer to: perform a first perfusion scan; monitor contrast level of the monitoring location based on projection data acquired during the first perfusion scan; responsive to the contrast level above a first threshold, perform an angiography scan; monitor contrast level of the monitoring location based on projection data acquired during the angiography scan; responsive to the contrast level below a second threshold, perform a second perfusion scan; monitor contrast level of the monitoring location based on projection data acquired during the second perfusion scan; responsive to the contrast level below a third threshold, end the single dynamic scan session; and reconstruct at least one diagnostic image based on one or more of the perfusion scan and the angiography scan data.

In a first example of the non-transitory computer-readable storage medium, the instructions further cause the computer to: calculate at least one perfusion parameter based on the projection data acquired during the perfusion scan. In a second example of the non-transitory computer-readable storage medium optionally including the first example, the instructions further cause the computer to perform a non-contrast scan of the head prior to identifying the monitoring location. In a third example of the non-transitory computer-readable storage medium optionally including one or more of the first and second examples, the monitoring location comprises multiple locations at different depths, and the contrast level is separately monitored at the multiple locations.

In yet another embodiment, a system comprises: an x-ray source that emits a beam of x-rays toward an object to be imaged; a detector that receives the x-rays attenuated by the object; a data acquisition system (DAS) operably connected to the detector; and a computer operably connected to the DAS and configured with instructions in non-transitory memory that when executed cause the computer to: during a single scan, process projection data received from the DAS to measure a contrast level; and automatically interleave at least two scan protocols during the single scan responsive to the contrast level.

In a first example of the system, the at least two scan protocols include an angiography protocol and a perfusion protocol, wherein automatically interleaving the at least two scan protocols comprises switching from an acquisition of the projection data according to one scan protocol of the at least two scan protocols to another scan protocol of the at least two scan protocols at least once during the single scan. In a second example of the system optionally including the first example, the instructions further cause the computer to reconstruct at least one diagnostic image based on projection data acquired with the angiography protocol. In a third example of the system optionally including one or more of the first and second examples, the system further comprises a display device, and the instructions further cause the computer to output the at least one diagnostic image to the display device for display. In a fourth example of the system optionally including one or more of the first through third examples, the instructions further cause the computer to calculate perfusion parameters based on projection data acquired with the perfusion protocol.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A method, comprising:
during a single scan of a scan subject in real-time,
processing acquired projection data to measure a contrast level;
responsive to the contrast level increasing above a first threshold, automatically switching the single scan from a first scan protocol to a second scan protocol;

responsive to the contrast level decreasing below a second threshold, automatically switching the single scan from the second scan protocol to the first scan protocol;

responsive to the contrast level decreasing below a third threshold, automatically ending the single scan; and adjusting a temporal sampling rate of the first scan protocol responsive to the contrast level, wherein the first threshold, the second threshold, and the third threshold comprise a threshold contrast level and a threshold rate of change of the contrast level.

2. The method of claim 1, wherein the first scan protocol includes a first scan region of the scan subject, and wherein the second scan protocol includes a second scan region of the scan subject, the second scan region larger than the first scan region.

3. The method of claim 2, wherein the first scan region includes a head of the scan subject and the second scan region includes the head and a neck of the scan subject.

4. The method of claim 1, wherein processing the acquired projection data comprises reconstructing at least one image slice based on the acquired projection data.

5. The method of claim 1, further comprising calculating the first threshold, the second threshold, and the third threshold based on a non-contrast scan performed prior to the single scan.

6. The method of claim 1, further comprising excluding performing a contrast bolus timing scan prior to the single scan.

7. The method of claim 1, further comprising adjusting transition time points of the single scan responsive to the contrast level.

8. The method of claim 1, further comprising separately measuring the contrast level in an artery and a vein positioned within a first scan region.

9. The method of claim 1, further comprising switching between the first scan protocol and the second scan protocol responsive to user input regardless of the contrast level.

10. A non-transitory computer-readable storage medium including executable instructions stored thereon that, when executed by a computer, cause the computer to:
identify a monitoring location of a patient;
administer a contrast agent to the patient;
perform a single dynamic scan session to acquire image data, wherein during the single dynamic scan session, the executable instructions further cause the computer to:
perform a first perfusion scan;
monitor a contrast level of the monitoring location based on projection data acquired during the first perfusion scan;
responsive to the contrast level above a first threshold, perform an angiography scan;
monitor the contrast level of the monitoring location based on projection data acquired during the angiography scan;
responsive to the contrast level below a second threshold, perform a second perfusion scan;
monitor the contrast level of the monitoring location based on projection data acquired during the second perfusion scan;
responsive to the contrast level below a third threshold, end the single dynamic scan session; and
reconstruct at least one diagnostic image based on one or more of the first perfusion scan, the second perfusion scan, and the projection data acquired during the angiography scan.

11. The non-transitory computer-readable storage medium of claim 10, wherein the executable instructions further cause the computer to calculate at least one perfusion parameter based on the projection data acquired during the first perfusion scan and the second perfusion scan.

12. The non-transitory computer-readable storage medium of claim 10, wherein the executable instructions further cause the computer to perform a non-contrast scan of a head prior to identifying the monitoring location.

13. The non-transitory computer-readable storage medium of claim 10, wherein the monitoring location comprises multiple locations at different depths, and wherein the executable instructions further cause the computer to separately monitor the contrast level at the multiple locations.

14. A system, comprising:
an x-ray source that emits a beam of x-rays toward an object to be imaged;
a detector that receives the x-rays attenuated by the object;
a data acquisition system (DAS) operably connected to the detector; and
a computer operably connected to the DAS and comprising non-transitory memory storing instructions that, when executed, cause the computer to:
during a single scan in real-time,
process projection data received from the DAS to measure a contrast level; and
automatically interleave at least two scan protocols during the single scan responsive to the contrast level, wherein automatically interleaving the at least two scan protocols comprises switching from an acquisition of the projection data according to a first scan protocol of the at least two scan protocols to an acquisition of the projection data according to a second scan protocol of the at least two scan protocols, and then back to the acquisition of the projection data according to the first scan protocol at least once during the single scan, wherein the first scan protocol is a perfusion scan protocol and the second scan protocol is an angiography scan protocol.

15. The system of claim 14, wherein the angiography scan protocol comprises one of a standard angiography protocol or a multi-phase angiography protocol.

16. The system of claim 15, wherein the computer is further configured with instructions in the non-transitory memory that, when executed, cause the computer to reconstruct at least one diagnostic image based on projection data acquired with the angiography scan protocol.

17. The system of claim 16, further comprising a display device, wherein the computer is further configured with instructions in the non-transitory memory that, when executed, cause the computer to output the at least one diagnostic image to the display device for display.

18. The system of claim 15, wherein the computer is further configured with instructions in the non-transitory memory that, when executed, cause the computer to calculate perfusion parameters based on projection data acquired with the perfusion scan protocol.

* * * * *